United States Patent [19]

Fischer et al.

[11] 4,140,901
[45] Feb. 20, 1979

[54] METHOD AND APPARATUS FOR PERFORMING THE SETTING-UP OF THE FAULT-SIGNAL EVALUATING CIRCUITRY OF AN APPARATUS WHICH DETECTS UNACCEPTABLE FAULTS IN GLASS BOTTLES, AND THE LIKE

[75] Inventors: Knut Fischer, Ahnsen; Gerhard Geisel, Bueckeburg, both of Fed. Rep. of Germany

[73] Assignee: Hermann Heye, Obernkirchen, Fed. Rep. of Germany

[21] Appl. No.: 791,600

[22] Filed: Apr. 27, 1977

[30] Foreign Application Priority Data

May 6, 1976 [DE] Fed. Rep. of Germany ....... 2620046

[51] Int. Cl.² ...................... G01D 21/04; G01N 21/22
[52] U.S. Cl. .................................. 250/223 B; 356/240
[58] Field of Search .................... 250/223 B; 356/165, 356/240

[56] References Cited

U.S. PATENT DOCUMENTS

| | | | |
|---|---|---|---|
| 3,479,514 | 11/1969 | Kidwell | 356/240 x |
| 3,687,559 | 8/1972 | Fischer | 356/240 |
| 3,942,001 | 3/1976 | O'Connor | 250/223 B |

Primary Examiner—Lawrence J. Dahl
Attorney, Agent, or Firm—Michael J. Striker

[57] ABSTRACT

The apparatus includes a photoelectric sensor associated with a predetermined zone of a hollow glass article to be examined for faults. During one testing operation, the photoelectric sensor successively detects all faults in that zone and generates for each a fault signal whose value is dependent upon the characteristics of the fault. The fault signals are applied to a threshold circuit which generates an output signal only when the fault-signal value exceeds a threshold-signal level. The setting-up procedure involves performing at least one preliminary testing operation upon a preselected sample or standard article having acceptable faults. Each threshold-circuit output signal automatically results in a circuit adjustment which reduces by a predetermined amount the extent to which the respective fault-signal value exceeds the threshold-signal level. The preliminary testing operation is performed repeatedly, until the largest-value fault signal generated during one testing operation has a value slightly below the threshold-signal level, whereupon the testing apparatus has been properly set-up automatically. Thereafter, testing operations are performed upon articles whose eventual faults or flaws are not yet known to be acceptable.

18 Claims, 10 Drawing Figures

METHOD AND APPARATUS FOR PERFORMING THE SETTING-UP OF THE FAULT-SIGNAL EVALUATING CIRCUITRY OF AN APPARATUS WHICH DETECTS UNACCEPTABLE FAULTS IN GLASS BOTTLES, AND THE LIKE

BACKGROUND OF THE INVENTION

The invention relates to a method and apparatus for performing the settingup of a fault-signal evaluating circuitry in an apparatus which detects the presence of unacceptable faults in and/or on a hollow body of transparent material.

The transparent material in question would in particular be glass or plastic. The faults to be detected would include cracks, contaminants, bubbles, holes, improperly formed mouths, as well as deviations from proper dimensions and configuration, such as tilted mouths, improper ovalness, anticlinal formations and improper length.

For example, cracks can be present in hollow glass articles in an almost unlimited variety of spatial orientations. However, in actual practice, cracks will tend to appear most often in certain zones of the article, determined by the production process involved. For each different type of hollow glass article, different typical crack orientations will predominate. There has been no reliable, simple and automatable procedure for locating all cracks in the series of hollow glass articles produced in a production run irrespective of type of article and types of cracks and of general applicability, such as for example impact and acoustical detection methods.

U.S. Pat. No. 3,687,559 discloses an optical method of detecting faults in hollow glass articles. A plurality of light beams are deflected onto respective zones of a hollow glass article to be tested. Photoelectric transducers are positioned in association with these zones, and if located in the dark receive light signals produced by a fault. An idealized crack forms, for example, a reflecting plane. A light source of fixed spatial orientation determines relative to this plane the location for the photoelectric transducer. If the orientation of the crack is different, the light source and/or transducer must be differently positioned. This applies to each zone of the hollow glass article to be examined. Because faults are most often located within the body of glass itself, there occurs in addition to reflection effects a refraction of the test light beam at the air-glass and glass-air interfaces, unless the test beam is incident normal to the surface of the hollow glass article. This refraction effect still further complicates the problem of properly performing the setting-up of the apparatus. Because of the innumerable possibilities as to the shapes of the faults and their orientations, one must limit oneself in actual practice to certain critical zones on the hollow glass body. Nevertheless, because of increasingly demanding industrial standards with respect to fault detection, an ever-growing number of light sources and photoelectric transducers is being required.

According to one prior-art setting-up technique, each of this plurality of testing channels in a single testing apparatus must be adjusted by a set-up technician possessed of exceptional aptitude for the visualization of geometrical and optical relationships and having furthermore considerable electronics expertise, who properly adjusts the positions and orientations of testing-channel components, selects proper sensitivity levels, and so forth. The task of such a set-up technician is greatly complicated by the fact that faults located in a zone associated with one testing channel of the apparatus may have an effect upon the detection of faults in zones associated with others in the testing channels. In addition, the industry seeks more and more to be able to detect smaller and smaller faults, creating increasingly difficult demands as to sensitivity and precision of detection.

SUMMARY OF THE INVENTION

It is a general object of the invention to provide a new way of performing the setting-up of the fault-signal evaluating circuitry of a testing apparatus of the type in question, even in the case of multi-channel apparatuses each of whose channels has a separate respective fault-evaluating circuit, the new procedure being simpler, quicker and more reliable than what is known in the prior art. Additionally, it is an object of the invention to provide a novel setting-up procedure which lends itself to at least partial automation. Furthermore, the novel setting-up procedure is to take into account the increasingly stringent demands being made in industry with respect to high sensitivity and precision of fault detection.

These objects can be met by providing the evaluating circuit of the at least one or each testing channel with a respective threshold circuit to which are applied the fault signals generated during the performance of a preliminary testing operation upon a preselected standard hollow article whose faults have been determined in advance to be within acceptable limits. Each fault signal whose value exceeds the threshold-signal level of the threshold circuit causes the latter to generate a threshold-circuit output signal. Each output signal is utilized, during one or a series of such testing operations, to repeatedly reduce the extent to which the fault-signal value exceeds the threshold-signal level, until finally the largest-value fault signal generated during one complete preliminary testing operation has a value just below the threshold-signal level.

The standard hollow article used for the one or more preliminary testing operations during setting-up can be taken from the current production run and examined to determine that its faults are within acceptable limits. To increase the precision of the standard which is being established by the setting-up procedure, these preliminary testing operations could be performed upon a plurality of such standard articles in succession.

If this setting-up of the fault-signal evaluating circuitry were not performed, then the evaluating circuitry would operate at maximum sensitivity — i.e., even the most minute faults, as well as even electrical interference signals, would result in the production of threshold-circuit output signals commanding automatic ejection of the article being tested. Using the novel setting-up procedure disclosed herein — which as explained below can be performed automatically in response to manual activation of a set switch — the sensitivity of the fault-signal evaluating circuitry is decreased from the maximum value in a stepwise fashion, until such time as the fault signals generated in response to detection of the acceptable faults in the preselected standard article are no longer capable of causing the evaluating circuitry to activate the reject ejector. Upon completion of the setting-up procedure, the testing apparatus permits all subsequently tested hollow articles to pass through, if their faults produce fault signals whose value is below the threshold-signal level of the threshold circuit.

In general, the performance of the complete setting-up procedure requires that a plurality of successive preliminary testing operations upon the preselected standard article be performed, particularly if the stepwise reductions in the difference between the threshold level and the value of the largest-value fault signal are to be kept very small. The fault signals may be produced in response to the performance of any repeatable type of measurement of hollow article faults, e.g., optical crack detection, density testing, and so forth.

The invention also seeks to provide an apparatus for the performance of the novel setting-up procedure.

According to one concept of the invention, the novel apparatus includes a multi-stage binary counter which counts the threshold-circuit output signals and which is provided at its output with a resistor network serving as a digital-to-analog converter. Such a binary counter is a relatively inexpensive circuit component and has the advantage that the information represented by its count is indefinitely registered, respectively stored, providing in addition to a stepping function also a storage function having particular significance with respect to the circuitry involved and the operations to be performed. The analog signal furnished by the digital-to-analog converter is used as a feedback signal to modify the fault-signal value and/or modify the threshold-signal level.

According to another concept of the invention, the threshold circuit and binary counter of each testing channel of the apparatus are connected together by a respective intermediate NAND-gate one of whose inputs is connected to a common set switch for all of the NAND-gates. The set switch is manually closed, to initiate the automatic setting-up procedure. The time during which the set switch is manually maintained closed determines the duration of the setting-up mode of operation, for all testing channels if a multi-channel testing apparatus is involved.

According to another concept of the invention, each threshold-circuit output is connected to the input of a respective monostable multivibrator, whose output is connected to an indicator element which provides a limited-duration indication when a high-value fault signal has triggered a threshold-circuit output signal. The indicator element could, for example, be a light-emitting diode with a light-up time interval of about 0.2 to 0.3 sec, established by an RC timing stage. In contrast, the durations of the actual fault signals are on the order of milliseconds. Accordingly, without the aforementioned indicator elements, these fault signals would not be perceivable by the human eye. Additionally, providing each testing channel with a respective indicator element provides a very simple and reliable way of monitoring the course of the automatic setting-up procedure, in particular for determining when the procedure has been completed in all channels. When all the indicator elements cease providing indications of in-progress setting-up operations, the technician can release the manual set switch, so that normal testing operations can begin.

According to one concept of the invention, each threshold circuit comprises an amplifier and a Schmitt trigger connected to the amplifier output, with the output of the aforementioned resistor network being fed back to an input of the amplifier.

If the threshold-signal level is not to be changed during setting-up, stepwise decrease of the D.C. voltage level of the amplifier (e.g., an operational amplifier) without change of gain can be effected by feeding back the analog feedback signal to the fault-signal input of the amplifier.

Alternatively, the amplifier can be of controllable gain, and the analog feedback signal can be used as a gain-control signal.

As a further possibility, each threshold circuit may comprise a two-input comparator, one input of which receives the fault signal, the other input of which receives the analog feedback signal, which latter would then alter the threshold-signal level.

According to a preferred concept of the invention, the fault-sensing means proper of each testing channel is connected to the respective fault-signal evaluating circuit through the intermediary of an optoelectronic coupler. The use of an optoelectronic coupler is particularly advantageous for establishing D.C. decoupling between the fault-sensing means proper and the associated fault-signal evaluating circuitry, particularly for example when the one is remotely located from the other and long connecting lines are involved, and also to reduce the effects of interference signals in the testing channels.

According to another concept of the invention, the testing apparatus is comprised of a stationary part and a rotary part. During testing operations, both for setting-up and also for normal testing, the rotary part rotates relative to the hollow body to be tested. The fault-sensing means of each testing channel would then include, as one possibility, a means mounted on the rotary part and operative for directing light onto the zone of the article associated with the respective testing channel, and also a photoelectric transducer likewise mounted on the rotary part and cooperating with light-emitting means to generate fault signals. Additionally, the photoelectric transducer of each testing channel has its output connected to the input of a respective amplifier mounted on the rotary part of the apparatus. The output of each such amplifier is electrically connected to a respective one of a plurality of slip rings, likewise mounted on the rotary part. Each slip ring is engaged by a respective electrical brush which feeds the fault-signals in the respective channel to the fault-signal evaluating circuitry of the channel. The testing apparatus actually incorporates a rectifier unit which converts A.C. voltage into D.C. voltage, which latter is applied to a D.C. voltage stabilizer furnishing stabilized D.C. operating voltage to all of the aforementioned amplifiers.

Such an expedient is known from the aforementioned U.S. Pat. No. 3,687,559. However, there the A.C. voltage is externally supplied and applied via a brush to a slip ring on the rotary part of the testing apparatus. This known approach has proved satisfactory for the sensitivity levels hitherto utilized in the art.

However, it is an additional object of the present invention to provide D.C. operating voltage in a way which does not create interference signal effects when higher-sensitivity fault detection is being employed, as in the present invention.

This object can be achieved by incorporating an A.C. generator within the testing apparatus itself. The rotor of the A.C. generator is mounted on the rotary part of the apparatus, and the stator on the stationary part. The integration of the A.C. generator right into the structure of the testing apparatus makes the transmission of A.C. voltage from outside the testing apparatus to circuitry located on moving parts of the apparatus unnecessary, and disposes of many interference-signal problems which would otherwise arise.

Another concept of the invention relates to the aforementioned use of optoelectronic couplers in the plural testing channels. The output of each optoelectronic coupler is connected to the input of the respective threshold circuit. However, each optoelectronic coupler also has an input current path including two input terminals. The first is connected to the respective one of the aforementioned electrical brushes. The second terminals of all the optoelectronic couplers are connected, in common, to an additional electric brush which is in sliding engagement with an additional slip ring mounted on the rotary part of the testing apparatus. This makes for D.C. decoupling and avoids many interference-signal problems which would otherwise arise in the context of this type of apparatus.

According to a further concept, the stator of the aforementioned integrated A.C. generator is comprised of two axially spaced multi-pole permanent-magnet rings, whose pole sections are located opposite alternating straight and crank-shaped soft magnetic rotor bars of the rotor, with one or a plurality of windings extending about the rotor in the spaces defined between the central portions of the straight bars and the radially offset central portions of the crank-shaped bars. This makes for a particularly simple construction capable of generating rather high power.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figures 1, 2:
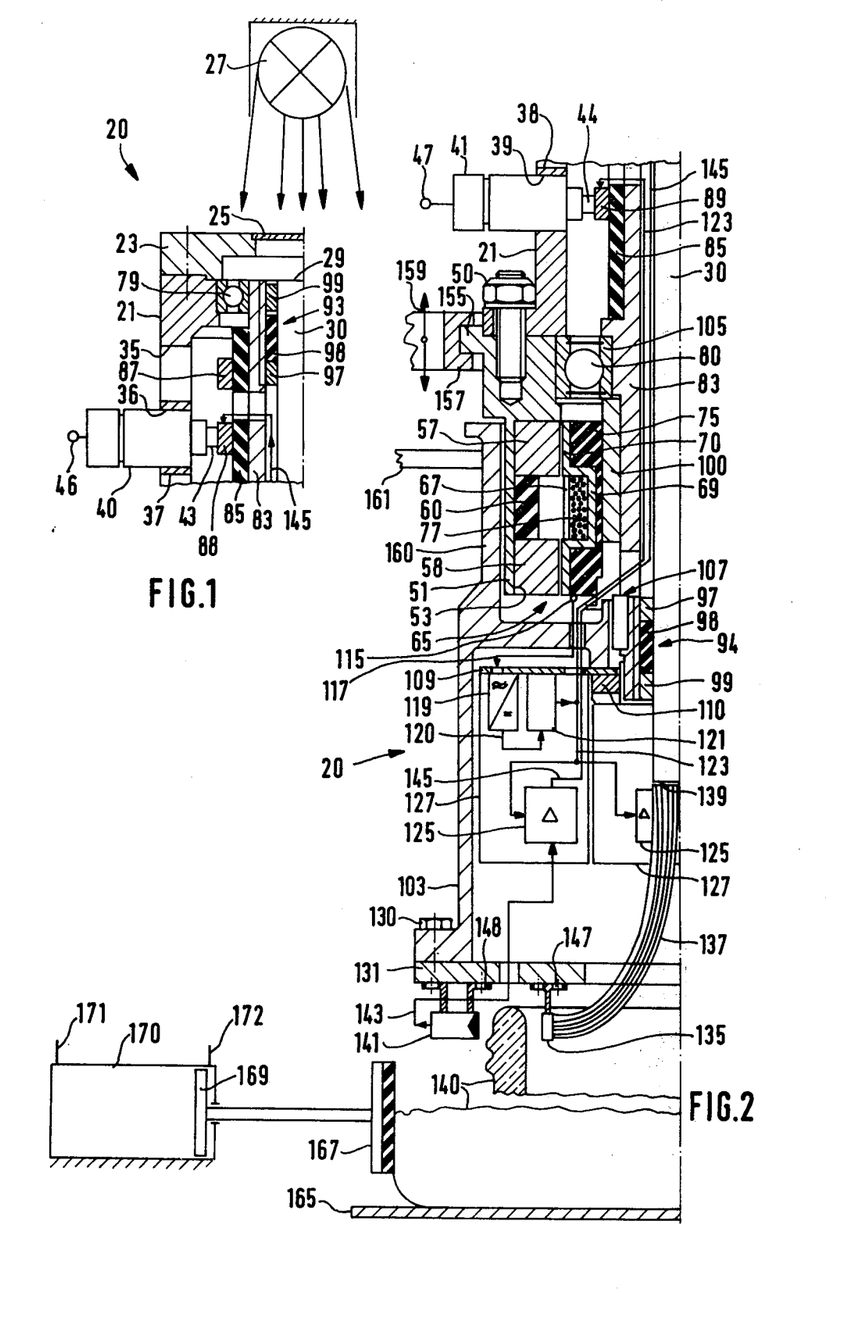
FIG. 1 is a partial longitudinal section through a testing apparatus.
FIG. 2 is a continuation of FIG. 1, showing the lower portion of the apparatus and also a hollow glass article in testing position.

FIGS. 1 and 2 depict a testing apparatus 20 which includes a non-rotating housing 21. The housing 21 is closed off at its top by a cover 23 provided with a central window 25. Window 25 permits light from a stationary light source 27 to fall upon the proximal end 29 of a monolithic rod 30 of a light-conducting material.

Housing 21 is provided with a plurality of axially successive openings; for the sake of simplicity of illustration, only the openings 35-39 are depicted in FIGS. 1 and 2. Mounted in each of these openings is a respective brush holder, e.g., 40 and 41 for respective electrical brushes 43 and 44. Each brush holder 40, 41 is provided with a respective connection terminal 46, 47.

A casing 51 is secured to the bottom of housing 21 by means of bolts and nuts 50. Fixedly inserted into a bore 53 in casing 51 are two permanent-magnet rings 57 and 58, maintained properly spaced apart by an intermediate ring 60 of magnetically non-conductive material. The permanent-magnet rings 57, 58 form the stator of an A.C. generator 65. The rotor of the generator is comprised of alternate straight bars 67 and crank-shaped bars 70 all made of soft magnetic material.

As illustrated, the two ends of each bar at any given time are located adjacent to opposite-polarity pole sections of the two permanent-magnet rings 57, 58. Likewise, the angular spacing between adjoining bars 67, 70 corresponds to the angular spacing between adjoining opposite-polarity pole sections on each ring 57, 58. The bars are embedded in a rotating ring 75 of generally U-shaped cross-section made of a magnetically non-conductive material, for example hard rubber. A bifilar widing 77 is disposed in the space intermediate the radially inwardly offset central portions 69 of the crank-shaped bars 70 and the central portions of the straight bars 67.

The upper parts of the housing 21 and of the casing 51 are provided with grooved ball bearings 79, 80, respectively, for a rotating interior pipe 83. The outer surface of interior pipe 83 is provided with a sleeve 85 of electrically non-conductive material. The insulator sleeve 85 mounts a plurality of slip rings, e.g. 87, 88, 89, which engage respective ones of the electrical brushes, e.g. 43 and 44.

The light-conductor rod 30 at its upper and lower ends is secured to the interior pipe 83 by means of clamping arrangements 93 and 94. Each clamping arrangement 93, 94 includes an abutment ring 97 screwed into the interior pipe 83, a rubber ring 98 supported thereon, and a threaded clamping ring 99 which can be tightened to press against the rubber ring 98.

The ring 75 (upon which the rotor bars 67, 70 are mounted) is mounted on a sleeve 100. The sleeve 100 is axially pressed by a rotating casing 103 against the internal ring 105 of the ball bearing 80. The casing 103 is prevented from rotating relative to the interior pipe 83 by means of a keyway-and-key connection 107 and receives its axial stress via a concentric mounting plate 109 and nut 110 screwed to the bottom of the interior pipe 83.

By way of example, one of the two windings of the bifilar winding 77 is provided with a connection terminal 115, from which a line 117 extends through an opening in the mouting plate 109 to a rectifier stage 119 mounted on the mounting plate 109. The D.C. voltage furnished by rectifier stage 119 is applied via a line 120 to a D.C. voltage stabilizer stage 121, likewise mounted on the mounting plate 109. The stabilized D.C. voltage is applied, firstly, to the slip ring 89 via a line 123 which extends through a further opening in the mounting plate 109 and also through further openings in the casing 103, the sleeve 100 and the interior pipe 83, and is available at terminal 47. Additionally, the stabilized D.C. voltage is applied to amplifiers 125 via a line 123 as the operating voltage for the amplifiers. Each testing channel of the testing apparatus has associated with it a respective circuit board 127, these being mounted at the periphery of the mounting plate 109, with each circuit board carrying the respective one of the amplifiers 125.

A base plate 131 is screwed to the bottom side of casing 103 by means of screws 130. The base plate 131 mounts a plurality of light-exit windows, e.g., the one denoted 135, of respective light-conductive fiber bundles 137 (one shown) which each receive light from the distal end 139 of the light-conductor rod 30 and transmit such light. The light-exit window 135 of each light-conductive fiber bundle 137 directs light onto a respective zone of a hollow glass article 140 to be tested. If a fault is present in such zone, light is, for example, received by a cooperating photoelectric transducer 141 which generates a corresponding electrical fault signal. This fault signal is transmitted via a line 143 to the input of the respective amplifier 125, whose output is connected to the respective slip ring (here 88) via a line (here 145) which passes through the aforementioned openings. In this way, the fault signal is applied to the connection terminal 46 of the respective one of the testing channels. In FIG. 2, the small mounting brackets for the light-exit window 135 and for the photoelectric transducer 141 have elongated holes 147, 148 and are mounted in place securely by adjusting screws which can be released or otherwise adjusted, in order to change the positions and orientations of the exit window 135 and transducer 141 relative to each other and relative to the hollow glass article 140.

The casing 51 at its upper end has a flange 155 at which the testing apparatus 20 is suspended by a holding structure 157 which is movable axially (as indicated by the double-headed arrow 159) down towards the hollow glass article 140 and then back up. However, this axial-movement capability is not necessary when the light-exit window 135 and the photoelectric transducer 141 can remain positioned above the mouth of the hollow glass article 140 during the entire testing cycle, e.g., for particular types fault detection.

The casing 103 is provided at its upper end with a recessed portion 160 about which is trained a drive belt 161 which effects rotation of the casing 103 and of the structure connected therewith.

The hollow glass article 140 is transported on a continuously operated conveyor belt 165 and brought into the testing position, wherein it is coaxial with the testing apparatus 20. This is accomplished by means of a holder 167 activated by the piston 169 of a double-acting cylinder-and-piston unit 170, the latter being provided with pressure-fluid ports 171 and 172. Cooperating with the holder 167 is a (non-illustrated) counterposition structure which engages the hollow glass article 140 from the side thereof diametrically opposite to the holder 167.

Figure 3:
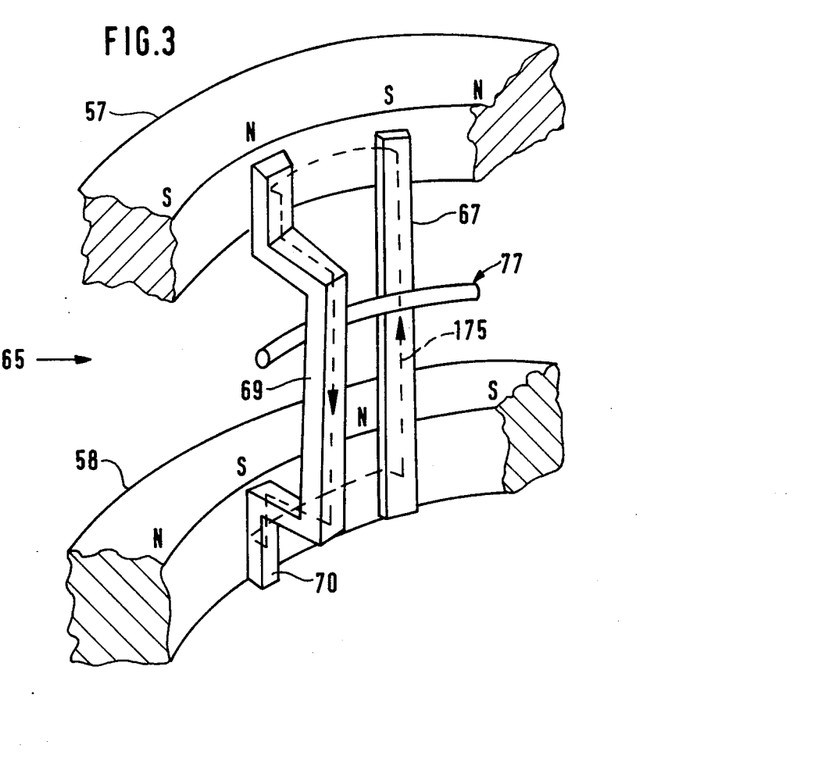
FIG. 3 is a partial perspective view of the A.C. generator structure of FIG. 2, on a larger scale.

FIG. 3 depicts on a larger scale and with greater detail the construction of the A.C. generator 65. The radially inward north- and south-pole sections of the permanent-magnet rings 57, 58 are denoted by N and S, respectively. The magnetic circuit 175 for magnetic flux is indicated by broken lines.

When the hollow glass article 140 is brought by the conveyor belt 165 into the testing position shown in FIG. 2, this is detected by a (non-illustrated) photoelectric detector unit. The latter produces an output signal which is applied, in FIG. 4, via a line 180 to the input of a Schmitt trigger 181. The $\bar{Q}$ output of Schmitt trigger 181 is connected via a line 183 to the R input of an RS (reset-set) flip-flop 185, utilized here as an auxiliary storage device. The Q output of Schmitt trigger 181 is connected via a line 187 to the clock input CL of a D (data) flip-flop 190. The S input of RS flip-flop 185 receives set signals via a connection terminal 193. The Q output of RS flip-flop 185 is connected via a line 195 to the D input of D flip-flop 190.

Figure 4:
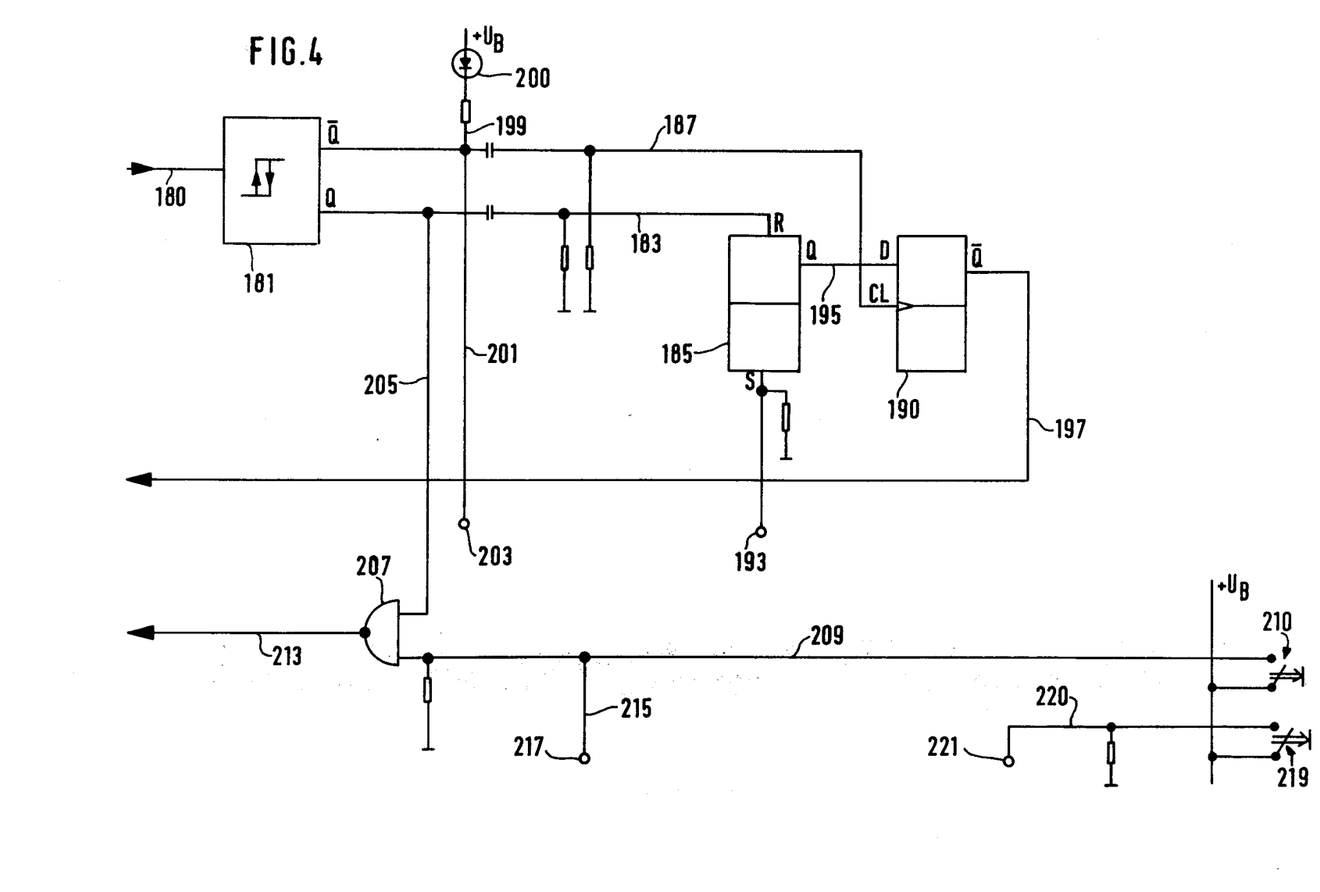
FIG. 4 is a circuit diagram of the first part of a fault-signal evaluating circuit.

The $\bar{Q}$ output of D flip-flop 190 is connected via a line 197 to a (non-illustrated) timer for the ejector which ejects off the conveyor hollow glass articles determined to have unacceptable faults. This ejector is per se conventional.

Line 187 is connected via a branch line 199 to a light-emitting diode 200, which lights up as long as the presence of a hollow glass article 140 at the testing position continues to be detected by the aforementioned (non-illustrated) photodetector unit. A further branch line 201 branching off line 187 is connected to a connection terminal 203.

A branch line 205 of line 183 is connected to one input of a NAND-gate 207, whose other input is connected via a line 209 to a manually activatable set switch 210. The output of NAND-gate 207 is connected via a line 213 to a (non-illustrated) timer which controls the operation of the holder 167, and is also connected to a (likewise non-illustrated) timer which controls the vertical motion of the testing apparatus 20. Both the testing apparatus 20 and the holder 167 stay in their operative positions for as long as the set switch 210 is manually maintained closed, provided that a hollow glass article 140 has been detected as being present in the testing position. A branch line 215 of line 209 leads to a connection terminal 217. Alongside the set switch 210 there is provided a reset switch 219 connected via a line 220 to a connection terminal 221.

Figure 5:
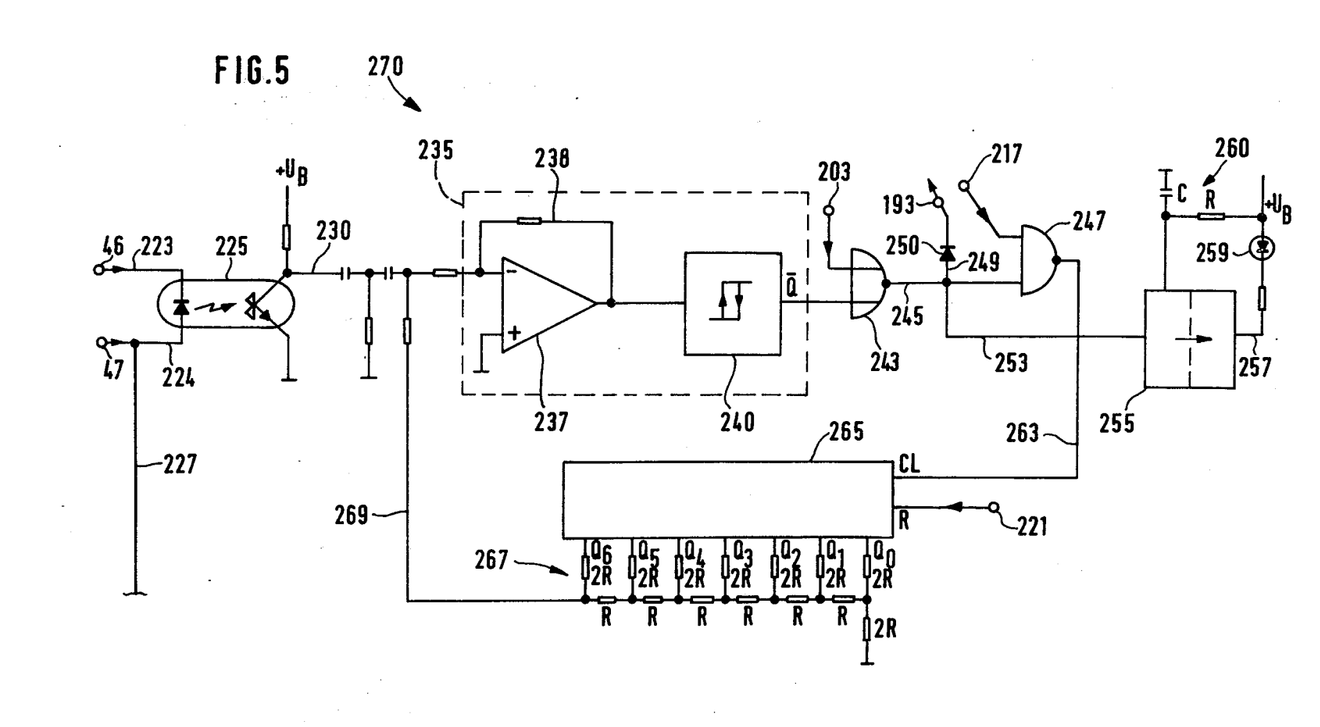
FIG. 5 is a circuit diagram of a first embodiment of the second part of the evaluating circuit.
Figures 7, 8:
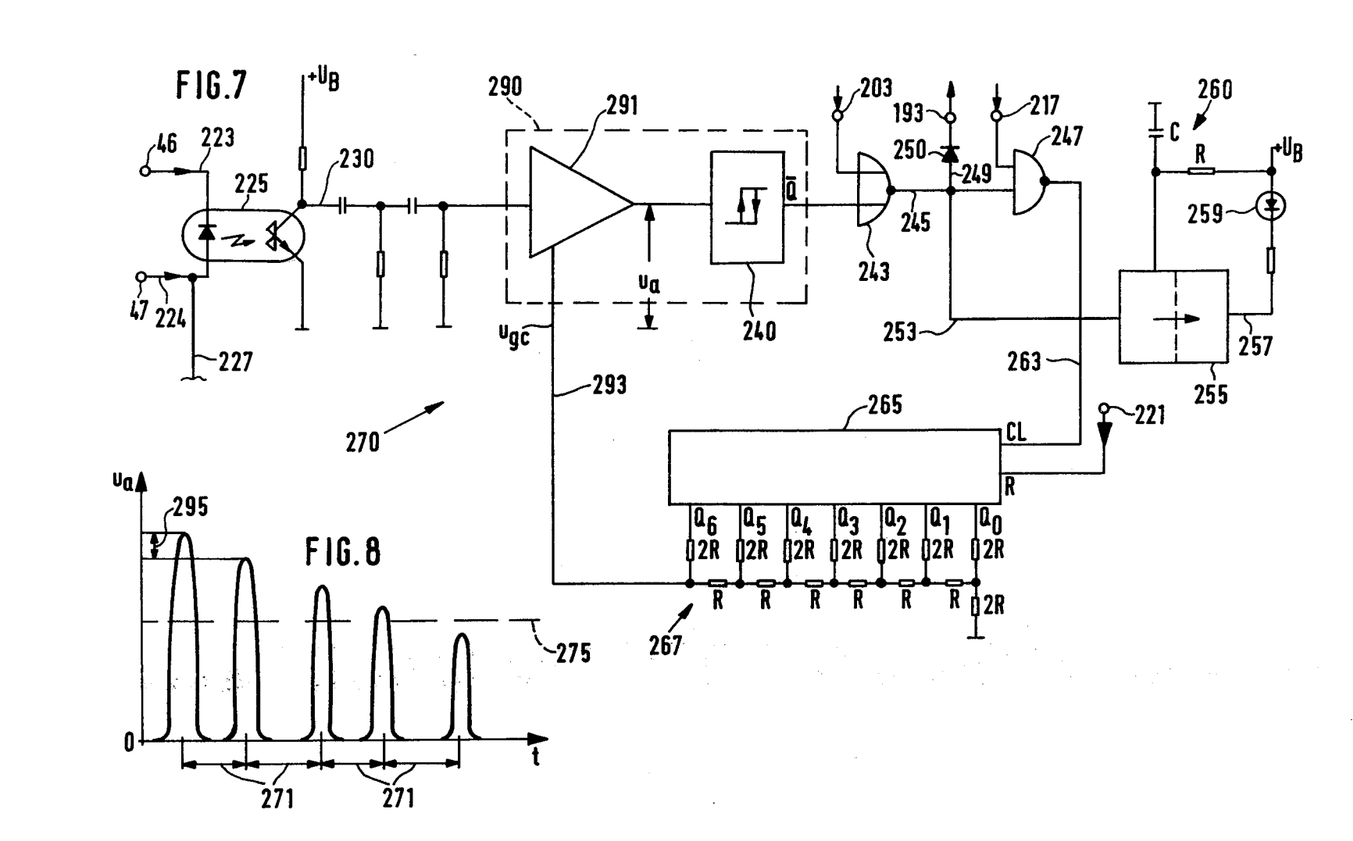
FIG. 7 is a circuit diagram of a second embodiment of the second part of the evaluatiing circuit.
FIG. 8 is a voltage-versus-time diagram for the circuit of FIGS. 4 and 7.
Figures 9, 10:
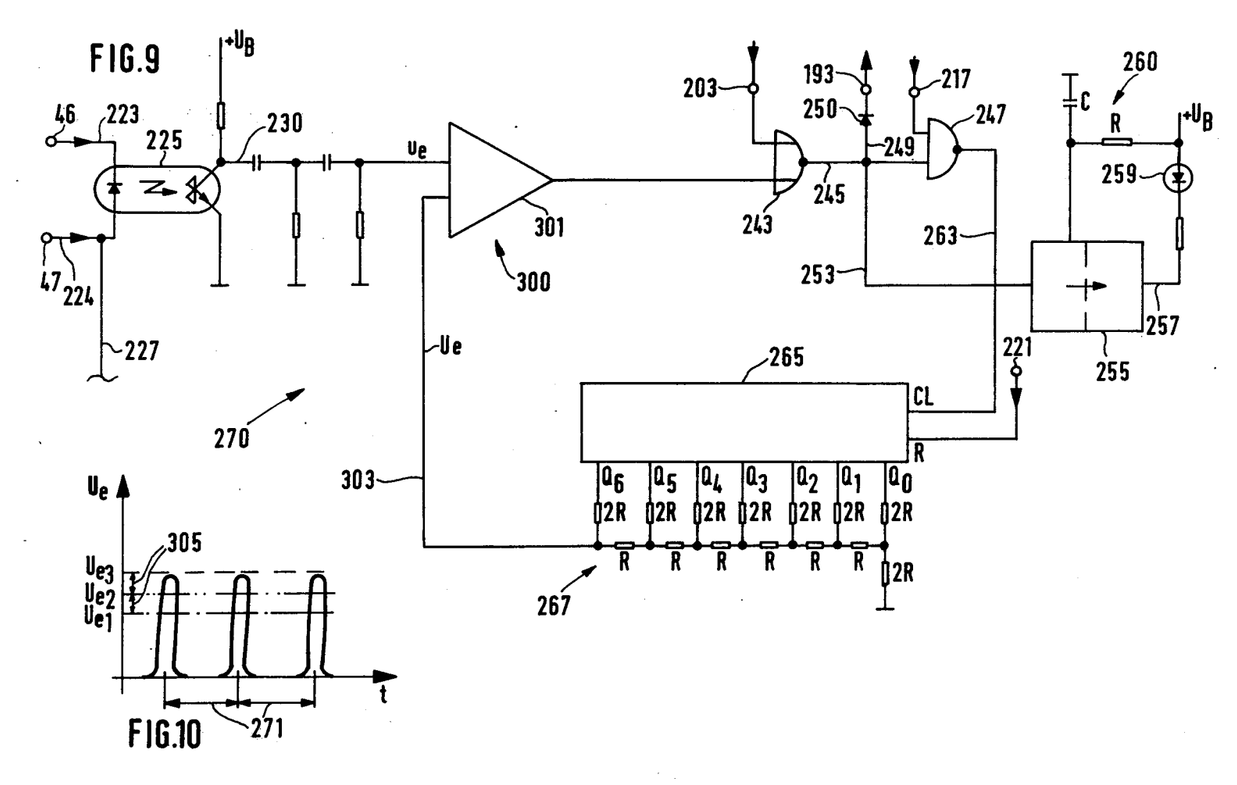
FIG. 9 is a circuit diagram of a third embodiment of the second part of the evaluating circuit.
FIG. 10 is a voltage-versus-time diagram for the circuit of FIGS. 4 and 9.

In FIG. 4 and in FIGS. 5, 7 and 9, still to be referred to, $U_B$ denotes the operating voltage of the circuitry.

As shown in FIG. 5, the connection terminals 46, 47 are connected by respective lines 223, 224 to an optoelectronic coupler 225. Quiescent current is always flowing through the current path defined by lines 223, 224 and the light-emitting element of the coupler 225; accordingly, there is a corresponding quiescent light emission in the coupler. When, as a result of the reflection of light resulting upon detection of a fault in the glass article, a fault signal becomes superimposed upon the quiescent current on line 223, a corresponding modulation of the light emission within the optoelectronic coupler 225 occurs. The optoelectronic coupler 225 serves to provide D.C. decoupling between the rotating system and the stationary system of the testing apparatus. A branch line 227 of the line 224 similarly biases the (non-illustrated) optoelectronic couplers of whatever further testing channels are provided in the apparatus, if any.

The output of optoelectronic coupler 225 is connected via a fault-signal line 230 to a threshold circuit 235 comprised of an operational amplifier 237 provided with a negative feedback branch 238 and a Schmitt trigger 240. The output of Schmitt trigger 240 is connected to one input of a NOR-gate 243, whose other input is connected to the connection terminal 203 (FIG. 4). The output of NOR-gate 243 is connected via a line 245 to one input of a NAND-gate 247, whose other input is connected to the connection terminal 217 (FIG.

4). A branch line 249 of line 245 leads via a diode 250 to the connection terminal 193 (FIG. 4). A further branch line 253 of line 245 is connected to the input of a monostable multivibrator 255, whose output is connected via a line 257 to an indicator element 259, here a light-emitting diode. The duration of the indication provided by indicator element 259 upon receipt of a signal from the monostable multivibrator 255 is determined by a timing stage, here an RC stage 260.

The output of NAND-gate 247 is connected via a line 263 to the counting input CL of a binary counter 265. The R input of binary counter 265 is connected to the connection terminal 221 (FIG. 4).

Binary counter 265 is a multi-stage counter and in the illustrated embodiment has outputs $Q_0$ to $Q_6$, connected to a resistor network 267. The output of network 267 is connected via a feedback line 269 to the fault-signal line 230.

Figure 6:
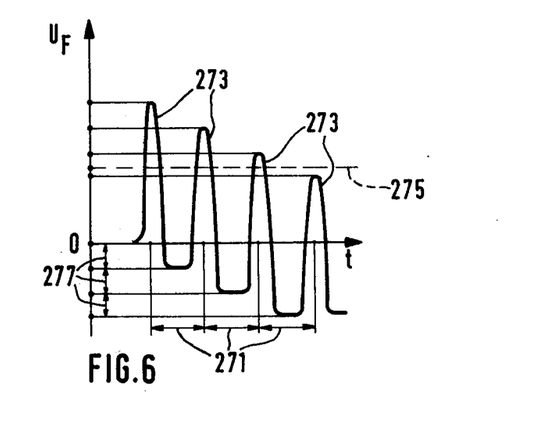
FIG. 6 is a voltage-versus-time diagram for the circuit of FIGS. 4 and 5.

FIG. 6 graphically depicts the variation in the fault voltage $U_F$ (fault signal) with respect to time for the evaluating circuit 270 of FIG. 5, during the setting-up of the evaluating circuit. During setting-up, there is positioned at the testing location of the testing unit a hollow glass body to be used as a standard of comparison; this standard glass body may, for example, be a glass bottle selected from a production series and determined in advance (for example by different means) to be of acceptable grade, i.e., to have faults which are acceptable.

The testing channel depicted in FIG. 5 is progressively adjusted with respect to one of these acceptable faults, e.g., a certain crack or scratch; during each successive rotation 271 (FIG. 6) of the testing apparatus 20 about the standard hollow body, a fault signal 273 is generated upon fault-signal line 230. As indicated in FIG. 6 by the broken line, the threshold circuit 235 in the testing channel has a fixed threshold voltage 275. At the start of the setting-up procedure, the first fault signal 273 extends very considerably above the threshold voltage 275, producing a threshold-circuit 235 output signal which advances the binary counter 265 by one count. As a result, the digital output signals of counter 265 are converted into an analog feedback signal, and this analog feedback signal is transmitted via feedback line 269 and the fault-signal line 230 to the operational amplifier 237, lowering the input voltage thereto by an amount 277 (FIG. 6). During successive rotations 271 of the testing apparatus 20, the peak of the fault voltage 273 is successively lowered, each time by the amount 277, until such time as the fault signal 273 (as shown at the right end of the graph in FIG. 6), has a peak value just below the threshold voltage 275. At that point, the automatic setting-up procedure for the testing channel in question is completed, and the threshold circuit of the testing channel produces no further output signal.

As a result, the light-emitting diode 259 ceases to be lit up; this affords the set-up technician the ability to visually monitor the extent to which the automatic setting-up procedure has progressed. Since each of the plurality of testing channels (if a plurality are employed) contains one respective such indicator element 259, the set-up technician need only wait until all of the indicator elements 259 have ceased to be lit up. At that point, the entire setting-up procedure for the entire evaluating circuit means 270 of all testing channels has been completed, and the manual set switch 210 can be released and accordingly permitted to reopen.

In response to opening of switch 210, the testing apparatus 20 is raised from its operative position to its inoperative position, and the holder 167 releases the standard hollow body for transport by the conveyor belt 165 away from the testing location. When now the next hollow glass article (i.e., the first one after the standard article) is delivered to the testing location and tested, only those faults in the article which produce fault signals 273 whose peaks are above the voltage threshold 275 — only those faults cause the threshold circuit 235 to produce an output signal. Now, because NAND-gate 247 is in disabled condition, such threshold-circuit output signals are not applied to binary counter 265 and do not advance the count thereon. Instead, such fault signals are applied, via the branch line 249, the connection terminal 193, the RS flip-flop 185, the D flip-flop 190 and line 197, to the activating means of the (non-illustrated) ejector.

In the subsequent Figures, components and quantities corresponding to those of FIGS. 5 and 6 are denoted by the same reference numerals and characters.

The circuit depicted in FIG. 7 includes a threshold circuit 290 in which the input of the Schmitt trigger 240 is connected to the output of a linear amplifier 291. The output of the resistor network 267 is here connected via a feedback line 293 to the gain-control input of amplifier 291. Accordingly, line 293 carries a gaincontrol voltage $u_{gc}$. During the course of the setting-up procedure, there is present at the output of the linear amplifier 291 an output voltage $u_a$ which is stepwise decreased in dependence upon the voltage $u_{gc}$. FIG. 8 depicts the variation of the amplifier output volage $u_a$ with respect to time during the course of the automatic setting-up procedure, and in particular the relationship of the peak values of successive fault signals to the threshold voltage 275 of the Schmitt trigger 240. Each rotation 271 of the testing apparatus 20 causes the amplitude of the fault signal to be reduced by an amount 295, until the amplitude of the fault signal is below the threshold voltage 275.

In the circuit shown in FIG. 9, the threshold circuit 300 comprises a comparator 301. One comparator input receives the fault voltage $u_e$ via the fault-signal line 230. The variation of the fault voltage with respect to time during the course of the setting-up procedure is graphically depicted in FIG. 10.

In this embodiment, the output of the resistor network 267 is connected via a feedback line 303 with the other input of the comparator 301. The voltage $U_e$ on line 303 defines the threshold voltage of the comparator 301. Each one-count advancement of the binary counter 265 causes the threshold voltage of comparator 301 to be increased by an amount 305 — i.e., during the first rotation 271 from $U_{e1}$ to $U_{e2}$, during the second rotation 271 from $U_{e2}$ to $U_{e3}$. As shown in FIG. 10, when the threshold voltage has been raised to $U_{e3}$ the setting-up procedure has been completed, because the fault signal generated in response to the fault in the standard article no longer exceeds the threshold voltage.

In the graphs depicted in FIGS. 6, 8, and 10, it is assumed for simplicity that the representative annular zone on the standard article being tested during the setting-up procedure contains a single acceptable fault or flaw. However, the annular zone associated with one such testing channel may contain a plurality of different flaws. In that event, the setting-up procedure is automatically performed with respect to that one of the flaws in the annular zone which produces the largest fault signal.

In the structure depicted in FIG. 2, the fault-sensing means 135, 141 proper is shown for only one testing channel; likewise, the complete circuit diagram of only one representative testing channel is shown. It is to be understood that if more than one testing channel is provided, each may have its own sensing means positioned and oriented to detect the faults in a respective zone of the hollow glass article to be tested.

It will be understood that each of the elements described above, or two or more together, may also find a useful application in other types of circuits and constructions differing from the types described above.

While the invention has been illustrated and described as embodied in a particular type of apparatus and circuitry for detection of faults in hollow glass articles and the like, it is not intended to be limited to the details shown since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an apparatus operative for detecting the presence of unacceptable faults in and/or on a hollow body of transparent material, at least one testing channel, each testing channel comprising:
    fault-sensing means operative for scanning a respective zone of a preselected hollow body having acceptable faults and producing a fault signal each time a fault is sensed;
    threshold circuit means receiving the fault signals and producing a threshold-circuit output signal each time a received fault signal exceeds a predetermined threshold level;
    and adjusting means usable for initially setting-up the apparatus, the adjusting means being connected to the threshold-circuit means and being operative in response to each thusly produced threshold-circuit output signal for decreasing by a predetermined limited extent the amount by which the fault signal exceeds the threshold level until such time as the highest-value one of the fault signals produced is below the threshold level.

2. The apparatus defined in claim 1, the adjusting means comprising means performing said decrease by altering the value of the fault signal.

3. The apparatus defined in claim 2, the adjusting means comprising means performing said decrease by altering the value of the fault signal without changing the threshold level of the threshold circuit means.

4. The apparatus defined in claim 3, the means altering the value of the fault signal including amplifying means for amplifying the fault signal and means for controlling the gain of the amplifying means.

5. The apparatus defined in claim 1, the adjusting means comprising means performing effecting said decrease by generating a further signal and superimposing the further signal upon the fault signal without altering the value of the fault signal.

6. The apparatus defined in claim 1, the adjusting means comprising means performing said decrease by changing the threshold level of the threshold circuit means.

7. The apparatus defined in claim 1, the adjusting means comprising means performing said decrease by changing the threshold level of the threshold circuit means without altering the value of the fault signal.

8. The apparatus defined in claim 1, each testing channel including optoelectronic coupling means coupling the output of the respective sensing means to the input of the respective threshold circuit means.

9. The apparatus defined in claim 1, the apparatus comprising a stationary part and a rotating part, the sensing means of each testing channel comprising photoelectric transducer means and means for directing light to the photoelectric transducer means both mounted on the rotating part, each testing channel including an amplifier mounted on the rotating part and having an input connected to the output of the respective photoelectric transducer means, a respective slip ring mounted on the rotating part and electrically connected to the output of the respective amplifier, a respective brush mounted on the stationary part in sliding engagement with the respective slip ring and means connecting the brush to the respective threshold circuit means; the apparatus furthermore including an A.C. generator comprising a rotor mounted on the rotary part and a stator mounted on the stationary part and operative for generating an A.C. voltage, means for converting the A.C. voltage into a D.C. voltage, a voltage stabilizer operative for converting the D.C. voltage into a stabilized D.C. operating voltage, and means for applying the stabilized D.C. operated voltage to the amplifier of each testing channel.

10. The apparatus defined in claim 9, the means connecting the brush of each testing channel to the threshold circuit means of the testing channel comprising an optoelectronic coupler having an output connected to the respective threshold circuit means and having first and second input terminals defining an input current path for the optoelectronic coupler, the first input terminal being connected to the respective brush, the apparatus furthermore including an additional slip ring mounted on the rotating part, means electrically connecting the slip ring to the output of the voltage stabilizer, an additional brush mounted on the stationary part in sliding engagement with the additional slip ring, and means electrically connecting the additional brush to the second input terminal of each optoelectronic coupler.

11. The apparatus defined in claim 9, the stator of the A.C. generator comprising two permanent-magnet rings axially spaced from each other with respect to the rotation axis of the rotating part of the apparatus, each permanent magnet ring having pole sections of opposite polarity alternating in the circumferential direction of the ring, the rotor of the A.C. generator comprising a plurality of straight bars and a plurality of crank-shaped bars, the bars being of soft magnetic material, the straight bars alternating with the crank-shaped bars in the circumferential direction of the rotor, and rotor winding means extending about the rotor in the space intermediate the central portions of adjoining ones of the straight and crank-shaped bars.

12. The apparatus defined in claim 5, the adjusting means comprising means performing said decrease without changing the threshold level of the threshold circuit means.

13. The apparatus defined in claim 1, the threshold-circuit means including a fixed-gain operational amplifier having an input connected to receive fault signals and having an output, and a fixed-threshold-level Schmitt trigger having an input connected to the output of the operational amplifier and having an output, the adjusting means including a binary counter connected to the output of the Schmitt trigger and operative for counting the number of fault signals exceeding the threshold level of the Schmitt trigger and digital-to-analog converter means comprising a resistor network, the digital-to-analog converter means being connected to the binary counter and responsive to the count on the latter and furthermore being connected to the input of the operational amplifier for stepwise decreasing the D.C. level of fault signals in dependence upon the changing count on the binary counter.

14. The apparatus defined in claim 1, the threshold-circuit means including a comparator having a signal input connected to receive fault signals and having a reference input for receipt of a reference signal determining the threshold level of the comparator, the adjusting means including a binary counter connected to the output of the comparator and operative for counting the number of fault signals exceeding the threshold level of the comparator and digital-to-analog converter means comprising a resistor network, the digital-to-analog converter means being connected to the binary counter and responsive to the count on the latter and furthermore being connected to the reference input of the comparator for applying to the reference input a reference signal which stepwise increases the threshold level of the comparator in dependence upon the changing count on the binary counter.

15. The apparatus defined in claim 13, furthermore including between the Schmitt trigger and binary counter of each testing channel a NAND-gate having a first input connected to the output of the respective Schmitt trigger and having an output connected to the respective binary counter, each NAND-gate furthermore having a second input; the apparatus furthermore comprising a manually activated switch connected to the second input of each NAND-gate operative for permitting each NAND-gate to transmit signals from the output of the respective Schmitt trigger to the respective binary counter.

16. The apparatus defined in claim 14, furthermore including between the comparator and binary counter of each testing channel a NAND-gate having a first input connected to the output of the respective comparator and having an output connected to the respective binary counter, each NAND-gate furthermore having a second input; the apparatus furthermore comprising a manually activated switch connected to the second input of each NAND-gate for permitting each NAND-gate to transmit signals from the output of the respective comparator to the respective binary counter.

17. The apparatus defined in claim 1, each testing channel furthermore including a monostable multivibrator connected to the output of the threshold-circuit means for producing brief pulses longer in duration than the threshold-circuit output signals, and indicator means connected to the output of the monostable multivibrator and activated by the brief pulses for producing visible indications that fault signals exceeding the threshold level are still being generated.

18. A method for setting-up an apparatus which detects the presence of unacceptable faults in and/or on a hollow body of transparent material, the apparatus comprising at least one testing channel, each testing channel including fault-sensing means operative for scanning a respective zone of such hollow body, the method comprising, in combination, the steps of
using the fault-sensing means to repeatedly scan a respective zone of a preselected hollow body having acceptable faults, the fault-sensing means producing a fault signal each time a fault is sensed;
transmitting the fault signals to the input of a respective threshold circuit means operative for producing a threshold-circuit output signal each time a received fault signal exceeds a predetermined threshold level;
and, in response to each thusly produced threshold-circuit output signal, decreasing by a predetermined limited extent the amount by which such fault signal exceeds the threshold level, until such time as the highest-value one of the fault signals is below the threshold level.

* * * * *